US00PP33802P3

(12) United States Plant Patent
Lyrene et al.

(10) Patent No.: US PP33,802 P3
(45) Date of Patent: Jan. 4, 2022

(54) BLUEBERRY PLANT NAMED 'COLOSSUS'

(50) Latin Name: ***Vaccinium corymbosum* L.**
Varietal Denomination: Colossus

(71) Applicant: Florida Foundation Seed Producers, Inc., Marianna, FL (US)

(72) Inventors: Paul M. Lyrene, Micanopy, FL (US); James W. Olmstead, Aptos, CA (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/935,768

(22) Filed: Jul. 22, 2020

(65) Prior Publication Data

US 2021/0029858 P1 Jan. 28, 2021

Related U.S. Application Data

(60) Provisional application No. 62/877,764, filed on Jul. 23, 2019.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

PP12,165 P2 10/2001 Lyrene
PP26,313 P2 1/2016 Lyrene et al.

*Primary Examiner* — Kent L Bell
(74) *Attorney, Agent, or Firm* — Dentons US LLP

(57) ABSTRACT

'Colossus' is a new and distinct southern highbush blueberry (*Vaccinium corymbosum* L.) variety distinguished at least by a low chilling requirement, vigorous, semi-bushy to semi-upright growth habit, good field disease resistance, and large, firm fruit that are sweet with a touch of acidity and exhibit small, dry picking scars and are suitable for mechanical harvest.

6 Drawing Sheets

Latin name of the genus and species of the plant claimed: *Vaccinium corymbosum* L.

Variety denomination: 'Colossus'.

BACKGROUND OF THE INVENTION

The invention relates to a new and distinct hybrid variety of southern highbush blueberry (*Vaccinium corymbosum* L.) plant 'Colossus' (alternatively designated as 'FL11-35'). 'Colossus', originated as a seedling that was generated from a cross performed in Gainesville, Fla. during February of 2008 between 'FL08-35' (unpatented), as the female (seed) parent, and 'FL04-103' (unpatented), as the male (pollen). The seedling was planted in a high-density field nursery in May of 2009, and the first fruit were evaluated in April of 2010. 'Colossus' was first asexually propagated during 2011 by softwood stem cuttings in Gainesville, Fla. After the second year of fruiting in the field, 'Colossus' was propagated by softwood stem cuttings during the spring of 2011 to establish an experimental 15-plant test plot for a variety test that was conducted during January of 2012 in Waldo, Fla. It was during this variety test that the experimental code 'Colossus' was assigned. Based on the growth, yield and fruit quality of this plot, 'Colossus' was repropagated by softwood stem cuttings and additional experimental test plots ranging from 5 to 45 plants were established for experimental research trials throughout Florida. These plots have been observed during flowering and ripening each year since establishment, and no mutations or off-type plants have been observed.

SUMMARY OF THE INVENTION

'Colossus' differs from its parents and all other known southern highbush blueberry plants. The following are the most distinguishing characteristics of 'Colossus' when grown under normal horticultural practices in Florida: (1) a low chilling requirement, particularly for the flower buds; (2) a vigorous, semi-bushy to semi-upright growth habit; (3) early ripening (from late March through late April, when grown as a deciduous plant in north central Florida and south Georgia); (4) concentrated ripening; and (5) large, firm, sweet berries with a touch of acidity that exhibit small, dry picking scars and are suitable for mechanical harvesting.

'Colossus' plants can be readily and unambiguously distinguished from those of its parents at least based upon early fruit yield. The early fruit yield exhibited by plants of 'Colossus' is significantly higher than that of either 'FL08-35' and 'FL04-103'.

Blueberry variety 'FL07-399' (U.S. Plant Pat. No. 26,313) is planted throughout the southeastern United States. Plants of 'Colossus' and 'FL07-399' can be readily and unambiguously distinguished at least based upon growth habit, and fruit characteristics. Plants of 'Colossus' display a semi-bushy to semi-upright and vigorous growth habit, while plants of 'FL07-399' display a vigorous upright spreading growth habit. Also, fruit of 'Colossus' is larger and firmer than those of 'FL07-399'.

Blueberry variety 'Emerald' (U.S. Plant Pat. No. 12,165) is planted throughout the southeastern United States. Plants of 'Colossus' and 'Emerald' can be readily and unambiguously distinguished at least based upon growth habit, the time at which their fruit is produced, and the ease with which their fruit can be mechanically harvested. Plants of 'Colossus' display a more upright and vigorous growth habit than those of 'Emerald'. Also, plants of 'Colossus' produce their fruit earlier than those of 'Emerald', and the fruit of 'Colossus' can be more effectively harvested by mechanical methods than that of 'Emerald'.

BRIEF DESCRIPTION OF THE DRAWINGS

'Colossus' is illustrated in the accompanying photographs, which show the plant's flowers, fruit, leaves, and form. Colors shown are as true as can be reasonably reproduced by photographic procedures and may differ from those cited in the detailed description, which accurately describe the colors of 'Colossus'.

DETAILED BOTANICAL DESCRIPTION

Figure 1:
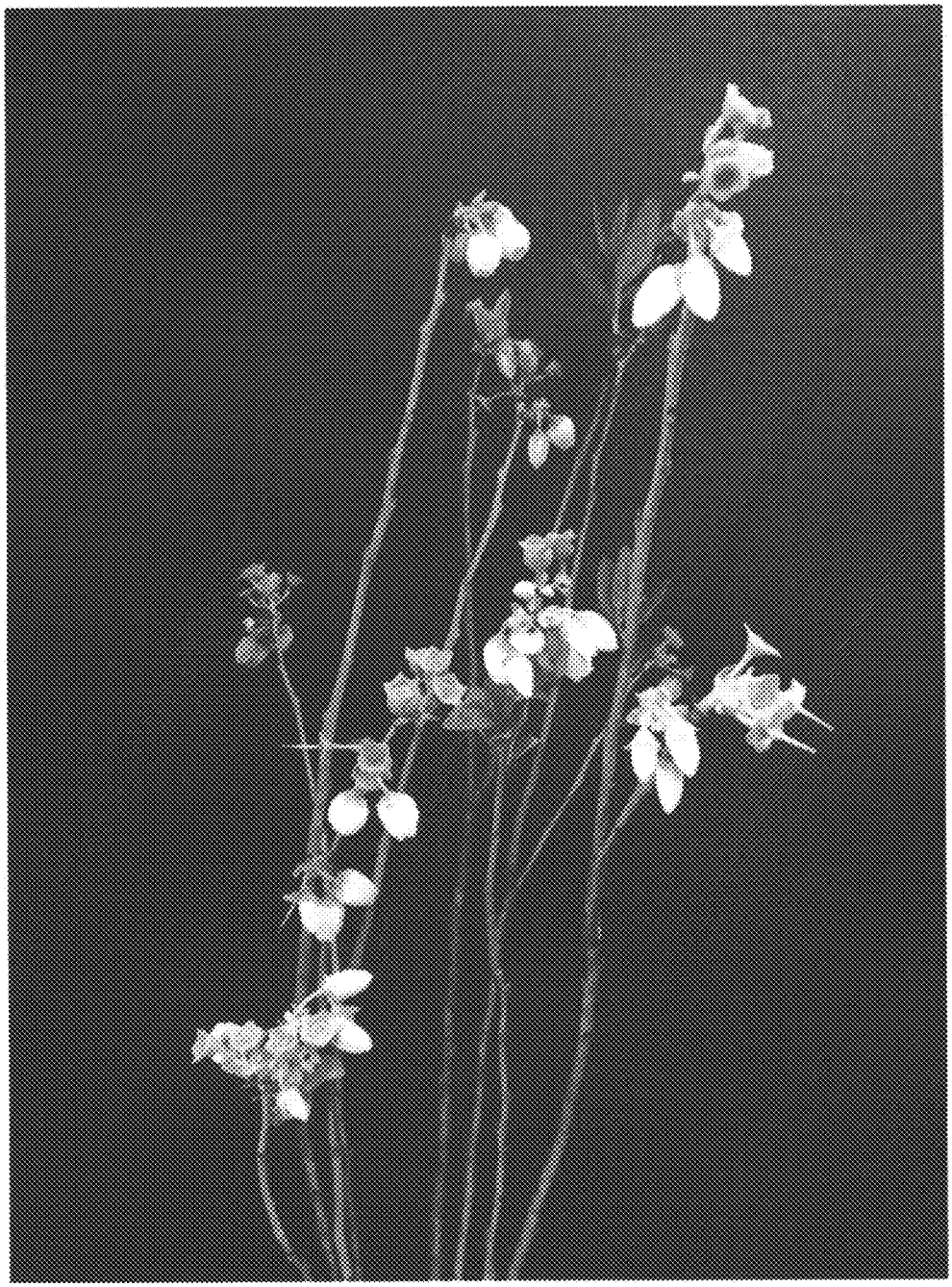
FIG. 1—Shows clusters of opening 'Colossus' flowers.
Figure 2:
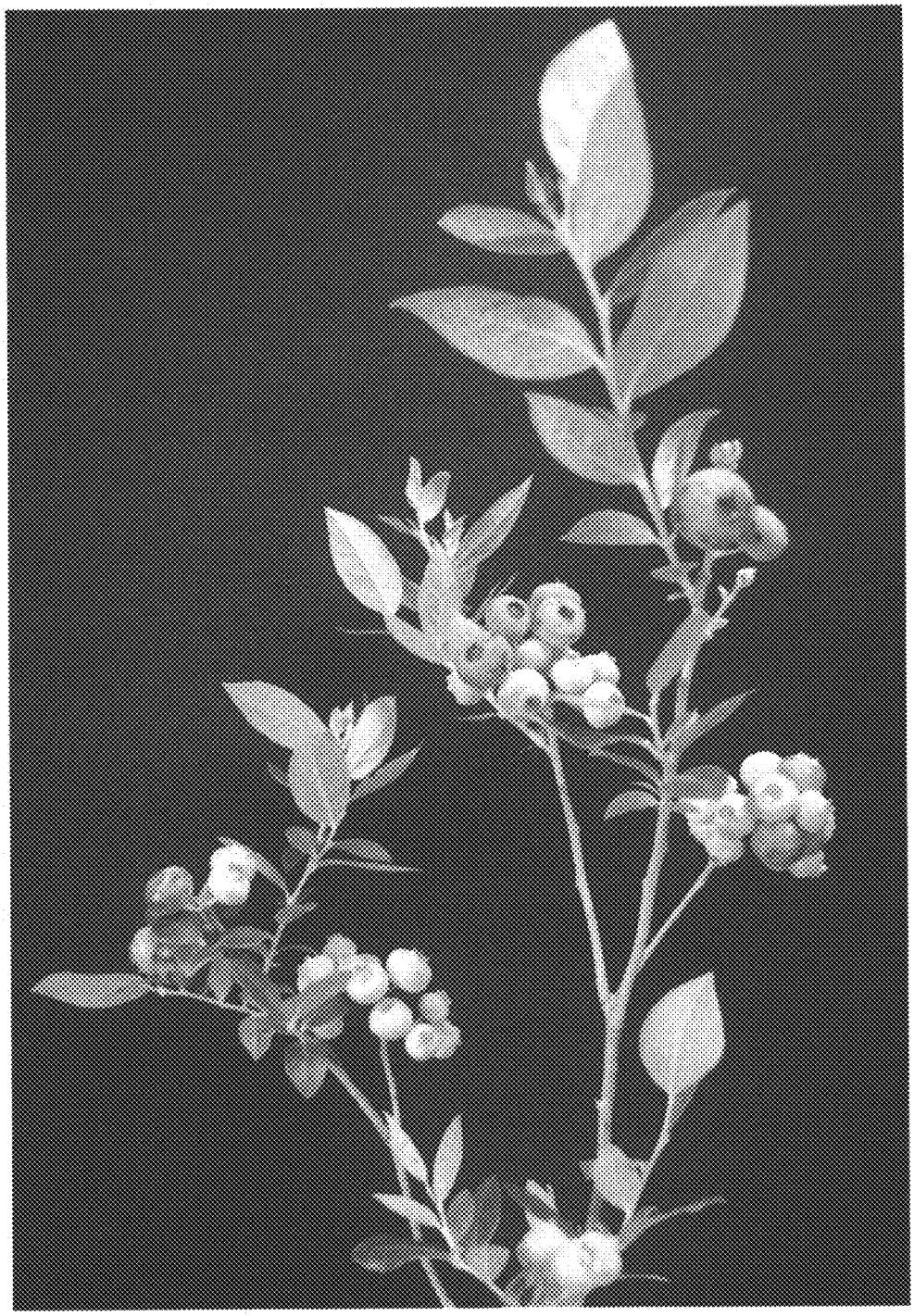
FIG. 2—Shows clusters of 'Colossus' berries during the fruit ripening season.
Figure 3:
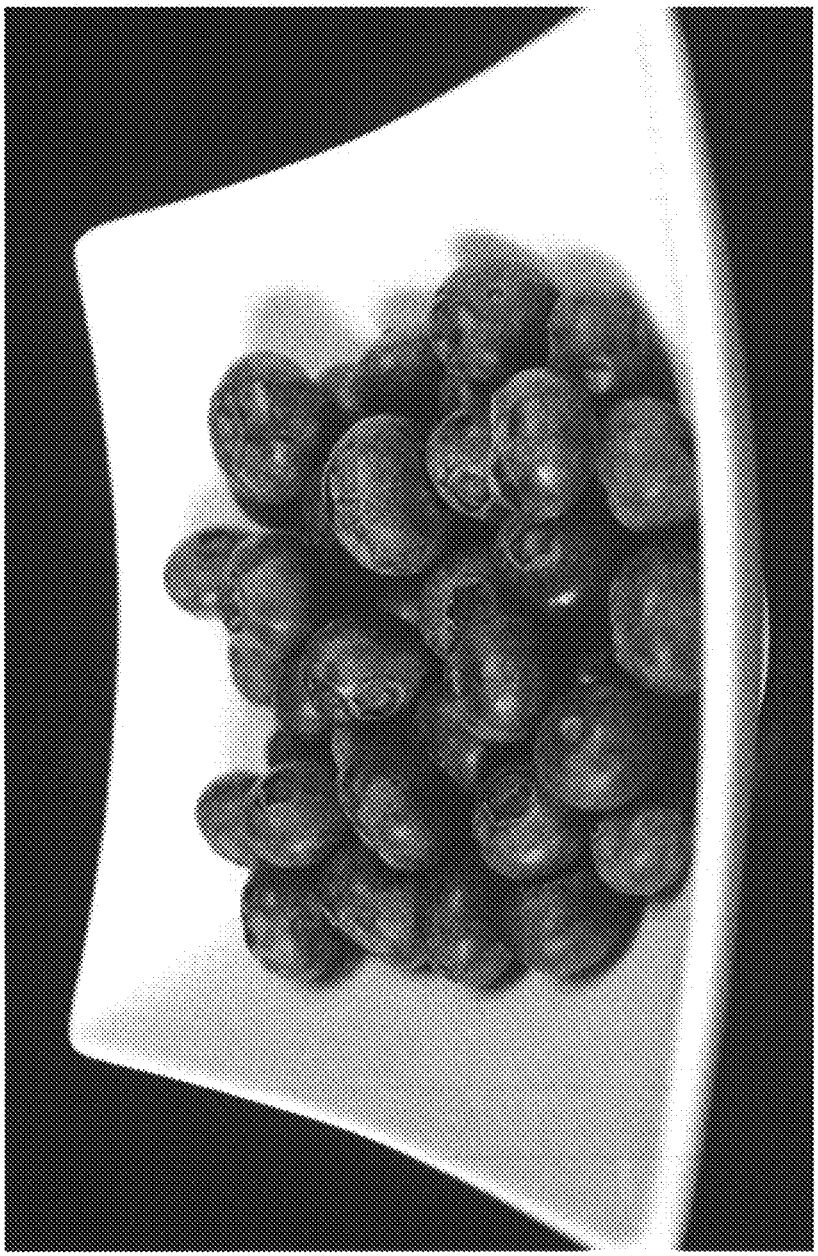
FIG. 3—Shows a close-up of harvested 'Colossus' berries.
Figure 4:
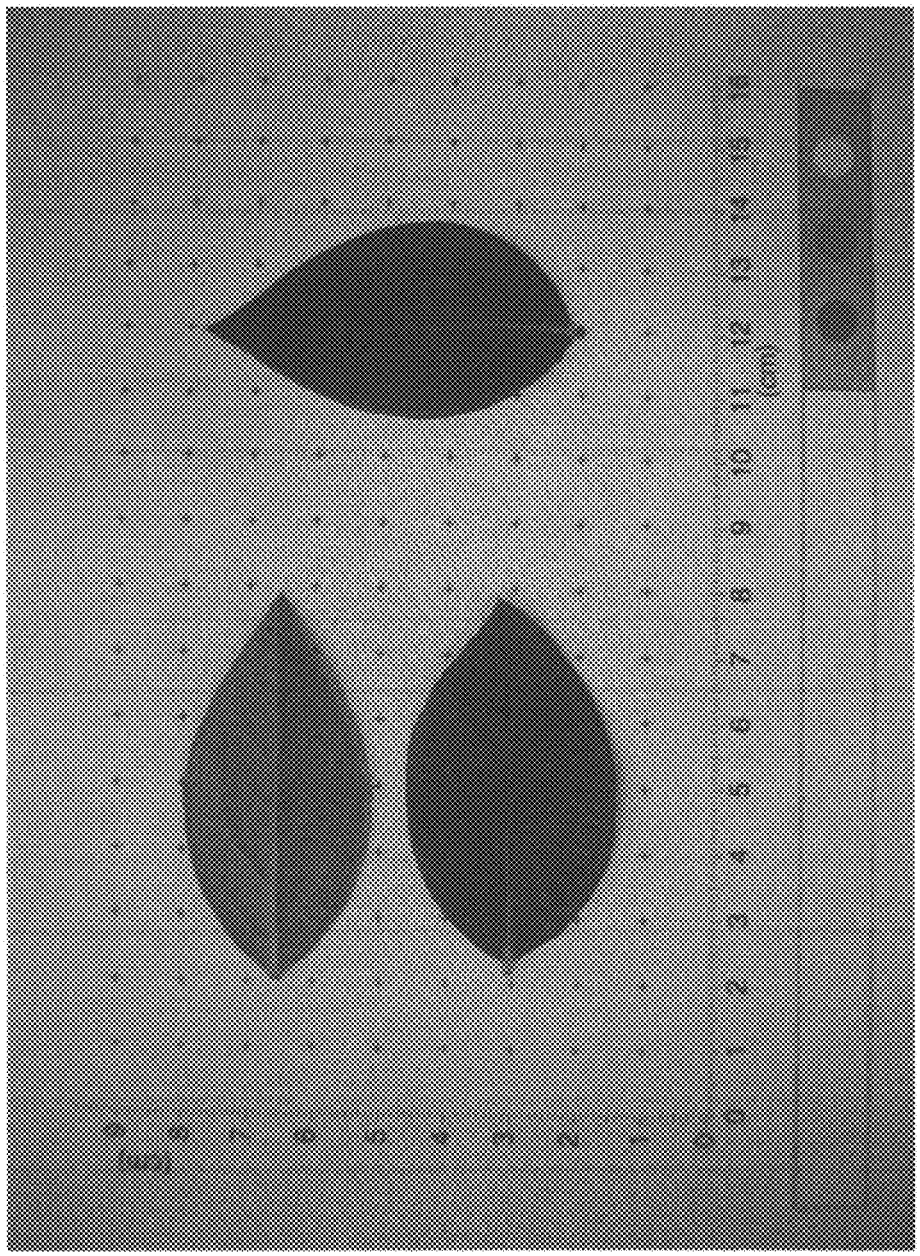
FIG. 4—Shows a close-up of mature 'Colossus' leaves with a scale bar.
Figure 5:
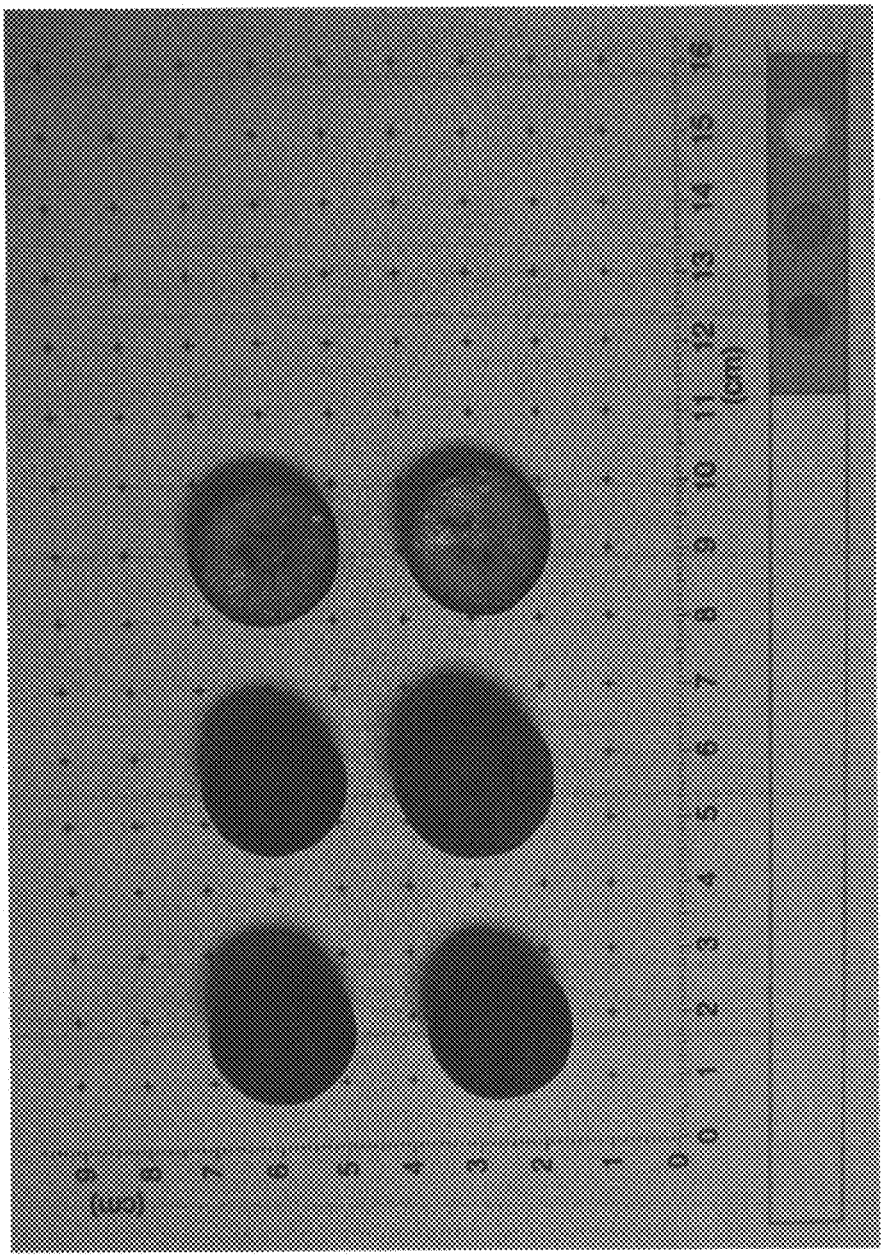
FIG. 5—Shows a close-up of mature 'Colossus' fruit with a scale bar.
Figure 6:
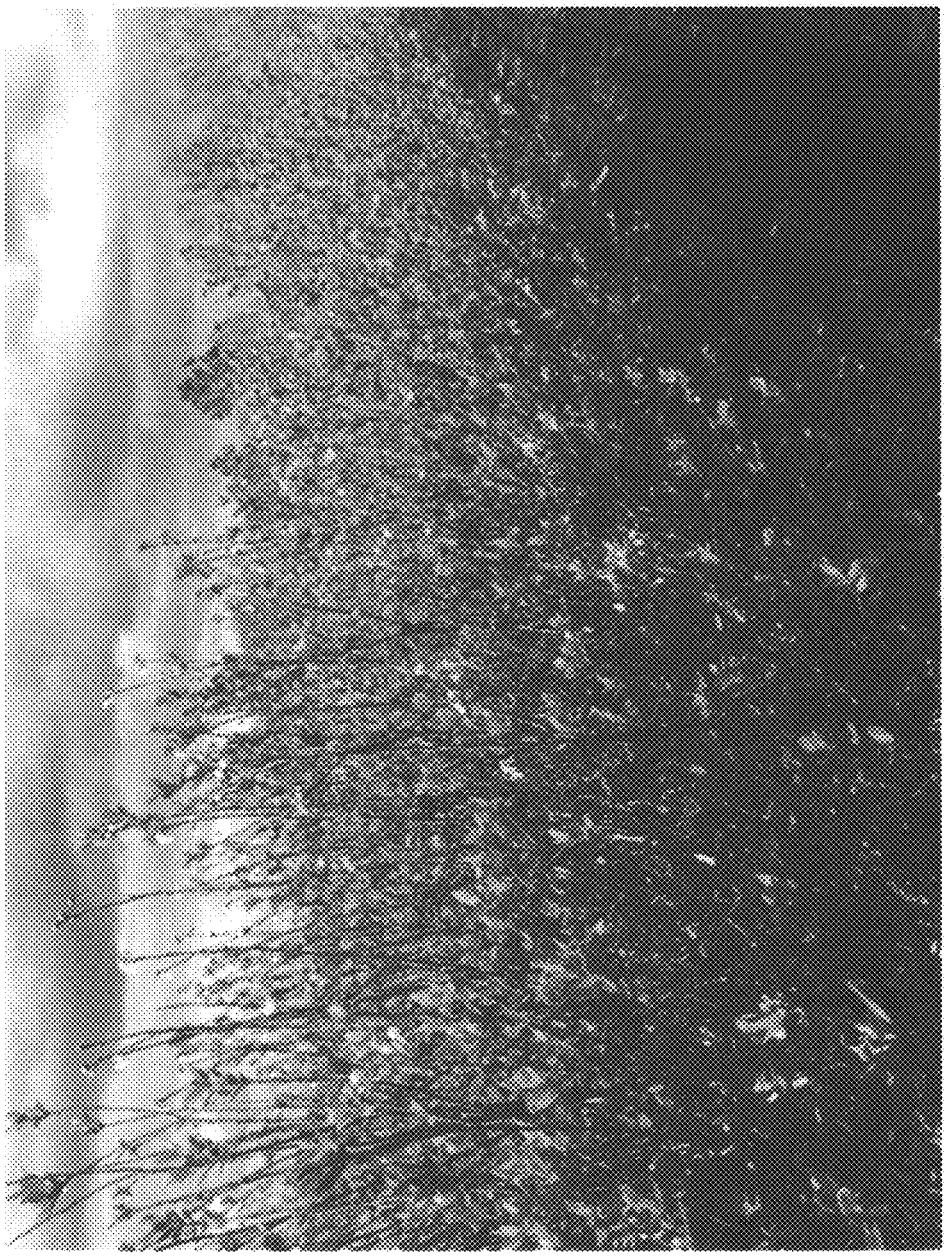
FIG. 6—Shows 5-year-old 'Colossus' plants during February, with their vigorous, semi-upright architecture.

The following detailed description sets forth distinctive characteristics of 'Colossus'. The data that define these characteristics were collected from asexual reproductions carried out in Florida. The plant history was taken on a plot of plants growing in an experimental trial near Waldo, Fla. Certain characteristics may vary with plant age. 'Colossus' has not been observed under all possible environmental conditions, and the measurements given may vary slightly when grown in different environments. Color descriptions are based on The Royal Horticultural Society (R.H.S.) Colour Chart by The Royal Horticultural Society, London, Sixth Edition, 2015. If any R.H.S. color designations below differ from the accompanying photographs, the R.H.S. color designations are accurate.

Classification:

*Family*.—Ericaceae.

*Botanical*.—*Vaccinium corymbosum* L.

*Common name*.—Southern Highbush Blueberry.

*Cultivar name*.—'Colossus'.

Plant:

*Plant vigor*.—Medium to high.

*Growth habit*.—Semi-bushy to semi-upright.

*Plant height* (*average*).—1.82 m (5-year-old plants).

*Plant spread* (*average*).—2.13 m (5-year-old plants).

*Flowers bud density along flowering twigs* (*number during January*).—Medium low.

*Twigginess*.—Medium-low.

*Tendency toward evergreenness*.—Medium-low.

*Productivity* (*when hand-harvested in northeast Florida*).—2.5 kg/season (5-year-old plants).

*Chilling requirement*.—150 hours below 7° C.

*Cold hardiness*.—Has been grown in temperate climates with extremely cold winter temperatures. Plants have survived winter freezes of −7° C. with minimal damage.

*Ease of propagation*.—Has only been propagated from softwood stem cuttings, where the rooting percentage is greater than 90% and comparable to other varieties.

Trunk and branches:

*Suckering tendency*.—Medium-low.

*Surface texture*.—Strong 12-month-old shoots (observed May of 2019): Slightly rough. 3-year-old and older wood: Medium-rough.

*Color*.—New twigs (field): Fan 4 grey group 201 pinkish grey D. 3-year-old, rough textured canes: Fan 4 brown group N200 light brownish grey C.

*Average internode length* (*strong, upright shoots measured in June*).—12.65 mm.

Petiole:

*Length*.—3.21 mm.

*Width*.—1.67 mm.

*Color*.—Fan 3 Yellow-Green Group N144 Strong Yellow-Green D.

*Texture*.—Smooth with no presence of pubescence.

Leaves:

*Length* (*average*).—4.909 cm.

*Width* (*average*).—2.315 cm.

*Shape*.—Elliptic.

*Leaf apex*.—Acute; with slight falcate.

*Leaf base*.—Elliptic.

*Margin*.—Entire.

*Surface color*.—Upper: Fan 3 green group 137 moderate olive green A. Lower: Fan 3 yellow green group 147 moderate yellow green C.

*Pubescence*.—Upper and lower surfaces and margins: Absent at all.

*Timing of vegetative bud burst* (*early, medium, late*).—Early.

*Relative time of leafing versus flowering* (*without midwinter hydrogen cyanamide treatment*).—Leaving occurs during flowering.

Flowers:

*Arrangement*.—Alternately along a moderate length leafing deciduous branch.

*Fragrance*.—None.

*Shape*.—Semi-urceolate, oblong.

*Flowering period*.—50% anthesis at Citra, Fla. on Feb. 15, 2019.

*Cluster*.—Medium-low.

*Number of flowers per cluster* (*average*).—3.

*Pedicel*.—Length at time of anthesis (average): 5.4 mm. Color at time of anthesis: Fan 3 yellow-green group N144 strong yellow green C, with Fan 4 greyed orange group 166 brownish orange C on the sun exposed side.

*Peduncle*.—Length at time of anthesis (average): 7.52 mm but highly variable. Color at time of anthesis: Fan 3 yellow-green group strong yellow green 144C, with Fan 4 greyed-red group moderate red 181B on sun exposed side.

*Calyx*.—Surface texture: Smooth with slight radiations. Diameter (average): 6.00 mm. Color (outer surface, visible at the time of anthesis without removing the corolla tube): Fan 3 green group 141 strong-yellowish green C to Fan 3 yellow-green group strong yellowish green D on calyx lobes.

*Corolla*.—Diameter (average): 7.68 mm. Length (average, from pedicel attachment point to corolla tip excluding the pedicel): 12.01 mm. Aperture diameter (average): 4.03 mm. Texture: Smooth with slight radiations. Color: Fan 4 white group 155 greenish white C. Anthocyanin coloration in corolla tube: None detected.

Reproductive organs:

*Style*.—Length (average, top of ovary to stigma tip): 6.44 mm. Color: Fan 3 yellow-green group 144 strong yellow green B. Location of tip of stigma relative to lip of the corolla: 1.10 mm below.

*Anthers*.—Color: Fan 4 greyed-orange group 163 deep orange yellow A. Pollen: High. Pollen germination: Greater than 90%. Color: Fan 1 yellow group 4 pale yellow green D. Filament length: 3.30 mm. Filament width: 1.15 mm.

*Self-fruitfulness*.—Low to medium. Planting in the field configurations that promote cross-fertilization with other southern highbush varieties is recommended for all southern highbush blueberry plants grown in Florida.

Fruit:

*Mean date of* 50% *harvest in Citra, Fla*.—Week 15.

*Diameter of calyx aperture* (*average, mature berry*).—0.51 cm.

*Size and shape of calyx lobes* (*mature berry*).—Absent to very small, erect to slight out curving. Shallow calyx basin.

*Pedicel length* (*average, ripe berry*).—8.0 mm.

*Detachment force for ripe berries* (*easy, medium, hard*).—Easy.

*Fruit cluster density* (*sparse, medium, dense*).—Medium to sparse.

*Number of berries per cluster* (*average*).—4.2.

*Fruiting type*.—On one-year-old shoots and current season's shoots.

Berry:

*Cluster* (*tight, medium, loose*).—Medium to loose.

*Weight* (*average, on well-pruned plants*).—Mean of 4.35 g.

*Height* (*average*).—1.46 cm.

*Width* (*average*).—2.07 cm.

*Shape*.—Oblate.

*Surface color of mature berries ripe on plant*.—Fan 2 violet-blue group 95 strong purplish blue C.

*Intensity of fruit bloom*.—High.

*Surface color of ripe berry after polishing*.—Fan 4 black group 203 bluish black C.

*Immature berry color*.—With bloom: Fan 3 green group 142 brilliant yellow green B. Without bloom: Fan 3 green group 142 brilliant yellow green B.

*Flesh color*.—Fan 3 yellow green group 145 light yellow green C.

*Surface wax*.—The surface wax on 'Colossus' has medium to high surface wax persistence.

*Pedicel scar*.—Small and dry, with an average size of 0.22 cm.

*Firmness*.—Very firm, with average of 261 g/mm.

*Flavor*.—Sweet, with some acid hints.

*Intensity of fruit sweetness*.—Medium.

*Texture*.—Good, with no stone cells present.

*Fruit storage quality*.—Fruit is firm and can be stored without shriveling, mold or loss of firmness for 3 weeks at 4° C.

Seeds:

*Color of dried seeds*.—Fan 4 Greyed-Orange group 165 Moderate Brown A.

*Weight of well-developed dried seeds*.—Mean of 2.72 mg.

*Length of well-developed dried seeds*.—Mean of 2.15 mm.

*Width of well-developed dried seeds*.—Mean of 1.25 mm.

Use: Produces southern highbush blueberries suitable for hand and machine harvest for the fresh fruit markets.

Resistance to diseases, insects, and mites: Has grown vigorously and shows good bush survival in the field. Twig blight (*Botryosphaeria* spp.) observed but lower than other cultivars, with almost no young plants dying soon after planting. Part of the 3% of selections that survived with over 95% of plants in the plot alive after 8 years in a high disease field planting. Reaction to the various fungal species that cause summer leaf spots (including rust) is lower than those of other southern highbush varieties. Fungicide applications may be needed after harvest to reduce foliar diseases and retain leaves into the fall for maximum flower bud set. Appears to be more tolerant than other southern highbush varieties to spider mites. Susceptibility to typical blueberry insect and mite pathogens such as spotted wing drosophila (*Drosophila suzukii*), blueberry gall midge (*Dasineura oxycoccana*), blueberry flower thrips (*Frankliniella* spp), and blueberry bud mite (*Acalitus vaccini*) appear similar to other southern highbush cultivars.

What is claimed is:

1. A new and distinct variety of southern highbush blueberry plant named 'Colossus', as illustrated and described herein.

* * * * *